(12) United States Patent
Wang et al.

(10) Patent No.: US 11,944,313 B2
(45) Date of Patent: *Apr. 2, 2024

(54) IMPLANTABLE EMBOLIZATION DEVICE

(71) Applicant: Covidien LP, Mansfield, MA (US)

(72) Inventors: Yihan Wang, Shanghai (CN); Victoria Schuman, Minneapolis, MN (US); Zhimin Fang, Shanghai (CN); Yapeng Xu, Shanghai (CN); Haitao Cao, Shanghai (CN); Zhipeng Chen, Shanghai (CN); Xiaojing Guo, Shanghai (CN); Shichang Wen, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/813,469

(22) Filed: Jul. 19, 2022

(65) Prior Publication Data

US 2022/0346802 A1 Nov. 3, 2022

Related U.S. Application Data

(63) Continuation of application No. 16/539,575, filed on Aug. 13, 2019, now Pat. No. 11,399,840.

(51) Int. Cl.
*A61B 17/12* (2006.01)
*A61F 2/01* (2006.01)
*A61F 2/06* (2013.01)

(52) U.S. Cl.
CPC .. *A61B 17/12113* (2013.01); *A61B 17/12145* (2013.01); *A61F 2/01* (2013.01);
(Continued)

(58) Field of Classification Search
CPC ........ A61B 17/12113; A61B 17/12145; A61B 17/1215; A61B 17/12154;
(Continued)

(56) References Cited

U.S. PATENT DOCUMENTS 4,994,069 A 2/1991 Ritchart et al.
5,522,822 A 6/1996 Phelps et al.
(Continued)

FOREIGN PATENT DOCUMENTS

EP 1960012 B1 8/2010
EP 3094269 A1 11/2016
(Continued)

OTHER PUBLICATIONS

"Controlled Precision Reliably Delivered," Concerto Coils, Medtronic, retrieved from: https://global.medtronic.com/xg-en/healthcare-professionals/products/cardiovascular/peripheral-embolization/concerto.html, Sep. 2017, 3 pp.
(Continued)

*Primary Examiner* — Kathleen S Holwerda
(74) *Attorney, Agent, or Firm* — Shumaker & Sieffert, P.A.

(57) ABSTRACT

In some examples, an embolization device includes multiple sections with three-dimensional non-helical structures when deployed at a vascular site. The multiple sections include a first section and one or more second sections that are smaller than the first section. The first section may have a deployed structure configured to anchor the device at a vascular site (e.g., a blood vessel) of a patient while each of the one or more second sections may be formed from loops that configured to pack and obstruct the vascular site. In some cases, the embolization device also includes a third section having a deployed configuration with multiple helical windings or loops is configured to anchor the embolization device at the vascular site.

21 Claims, 5 Drawing Sheets

(52) U.S. Cl.
CPC ... *A61B 2017/1205* (2013.01); *A61B 17/1215* (2013.01); *A61B 17/12154* (2013.01); *A61F 2/06* (2013.01)

(58) Field of Classification Search
CPC ..... A61B 2017/1205; A61B 2017/2212; A61F 2/01–2/014
See application file for complete search history.

(56) References Cited

U.S. PATENT DOCUMENTS

| | | | |
|---|---|---|---|
| 5,536,274 | A | 7/1996 | Neuss |
| 5,649,949 | A | 7/1997 | Wallace et al. |
| 5,733,329 | A | 3/1998 | Wallace et al. |
| 5,800,454 | A | 9/1998 | Jacobsen et al. |
| 6,033,423 | A | 3/2000 | Ken et al. |
| 6,117,157 | A | 9/2000 | Tekulve |
| 6,156,061 | A | 12/2000 | Wallace et al. |
| 6,432,134 | B1 | 8/2002 | Anson et al. |
| 6,551,340 | B1 | 4/2003 | Konya et al. |
| 6,790,218 | B2 | 9/2004 | Jayaraman |
| 6,860,893 | B2 | 3/2005 | Wallace et al. |
| 7,033,374 | B2 | 4/2006 | Schaefer et al. |
| 7,485,123 | B2 | 2/2009 | Porter |
| 7,488,332 | B2 | 2/2009 | Teoh et al. |
| 7,645,292 | B2 | 1/2010 | Porter |
| 7,879,064 | B2 | 2/2011 | Monstadt et al. |
| 8,007,509 | B2 | 8/2011 | Buiser et al. |
| 8,043,321 | B2 | 10/2011 | Elliott |
| 8,328,860 | B2 | 12/2012 | Strauss et al. |
| 8,414,634 | B2 | 4/2013 | Sekido et al. |
| 8,801,747 | B2 | 8/2014 | Strauss et al. |
| 9,055,948 | B2 | 6/2015 | Jaeger et al. |
| 9,089,405 | B1 | 7/2015 | Gulachenski et al. |
| 9,289,215 | B2 | 3/2016 | Strauss et al. |
| 9,393,021 | B2 | 7/2016 | Garcia et al. |
| 9,687,245 | B2 | 6/2017 | Molaei et al. |
| 9,795,389 | B2 | 10/2017 | Elliott |
| 9,993,252 | B2 | 6/2018 | Keeley et al. |
| 10,058,330 | B2 | 8/2018 | Fitz et al. |
| 10,064,747 | B2 | 9/2018 | Berez et al. |
| 10,081,048 | B2 | 9/2018 | Monetti et al. |
| 11,399,840 | B2 * | 8/2022 | Wang ............... A61B 17/12145 |
| 2002/0193825 | A1 | 12/2002 | McGuckin, Jr. et al. |
| 2004/0098023 | A1 | 5/2004 | Lee et al. |
| 2005/0090856 | A1 | 4/2005 | Porter |
| 2005/0107823 | A1 | 5/2005 | Leone et al. |
| 2006/0095071 | A1 | 5/2006 | Zhang |
| 2010/0010533 | A1 * | 1/2010 | Burke ............... A61B 17/1215 606/200 |
| 2010/0174301 | A1 | 7/2010 | Wallace et al. |
| 2013/0184658 | A1 | 7/2013 | Duncan |
| 2013/0331883 | A1 | 12/2013 | Strauss et al. |
| 2014/0128907 | A1 | 5/2014 | Hui et al. |
| 2015/0257765 | A1 | 9/2015 | Barkenbus et al. |
| 2016/0228127 | A1 | 8/2016 | Zhang et al. |
| 2017/0035436 | A1 | 2/2017 | Morita |
| 2017/0105738 | A1 * | 4/2017 | Suzuki ............. A61B 17/12031 |
| 2017/0189033 | A1 | 7/2017 | Sepetka et al. |
| 2018/0036012 | A1 | 2/2018 | Aboytes et al. |
| 2018/0104040 | A1 | 4/2018 | Bowman et al. |
| 2018/0325706 | A1 | 11/2018 | Hebert et al. |
| 2019/0015108 | A1 | 1/2019 | Maitland et al. |

FOREIGN PATENT DOCUMENTS

| | | |
|---|---|---|
| WO | 0193937 A2 | 12/2001 |
| WO | 2008112436 A2 | 9/2008 |
| WO | 2012155100 A1 | 11/2012 |
| WO | 2015109007 A1 | 7/2015 |
| WO | 2018053314 A1 | 3/2018 |
| WO | 2018073830 A2 | 4/2018 |

OTHER PUBLICATIONS

Gandhi et al. "Clinical Versatility of the Concerto ™ Detachable Coils in Peripheral Embolization," Insert to Endovascular Today, Sep. 2014, 5 pp.

International Preliminary Report on Patentability from International Application No. PCT/US2020/042352, dated Feb. 24, 2022, 7 pp.

International Search Report and Written Opinion of International Application No. PCT/US2020/042352, dated Oct. 27, 2020, 12 pp.

Prosecution History from U.S. Appl. No. 16/539,575, now issued U.S. Pat. No. 11,399,840, dated Jul. 20, 2021 through Apr. 11, 2022, 80 pp.

Van Rooj et al. "Packing Performance of GDC 360° Coils in Intracranial Aneurysms: A Comparison with Complex Orbit Coils and Helical GDC 10 Coils," AJNR Am J Neuroradiol 28:368-70, Feb. 2007, 3 pp.

Weisstein, "Polyhedron," retrieved from: http://mathworld.wolfram.com/Polyhedron.html, Wolfram Research, Inc. Mar. 25, 2019, 5 pp.

* cited by examiner

IMPLANTABLE EMBOLIZATION DEVICE

This application is a continuation of U.S. patent application Ser. No. 16/539,575, which was filed on Aug. 13, 2019, and is entitled, "IMPLANTABLE EMBOLIZATION DEVICE," the entire content of which is incorporated herein by reference.

FIELD

The present technology relates to implantable medical devices configured for embolizing a vascular site.

BACKGROUND

Implantable embolization devices may be used to embolize, e.g., occlude, a vascular site. Possible clinical applications include controlling bleeding from hemorrhages, reducing blood flow to tumors, and treating a diverse number of conditions including, for example, pathologies of the brain, the heart, and the peripheral vascular system. Among other examples, implantable embolization devices may be used to treat aneurysms, vascular malformations, arteriovenous fistulas, pelvic congestion syndrome, and varicoceles. An implantable embolization device may be configured to pack a vascular site in a patient, thereby reducing blood flow, promoting clotting, and eventually occluding the vascular site.

SUMMARY

In some aspects, this disclosure describes example embolization devices that include multiple sections with three-dimensional non-helical structures when deployed at a vascular site or other hollow anatomical structure of a patient. The multiple sections include a first section and one or more second sections that are configured to deploy into a smaller volume than the first section. For example, the multiple sections can include a first section and two or more second sections trailing the first section. In some cases, the different types of sections are configured to provide different features and/or capabilities. For example, in some examples, the first section may have a deployed structure configured to anchor the device in vasculature of a patient. As an example, the first section may define loops that are configured to form a scaffold inside a hollow anatomical structure (e.g., a blood vessel lumen) that holds the device in place. In some cases, the second sections define loops that are smaller than the first section loops and that can thus fit within and pack the scaffolding defined by the first section to obstruct the hollow anatomical structure.

Some example embolization devices include a third section having a deployed configuration that is different from the first and second sections. For example, an embolization device may include a third section, used for example at a leading end, that has multiple helical windings or loops configured to anchor the embolization device at a target site with a relatively high fluid (e.g., blood) flow rate anatomies.

In some aspects, this disclosure further describes assemblies for embolizing a vascular site. Also discussed are methods for delivering and deploying example embolization devices, as well as methods for forming example embolization devices.

Clause 1: In some examples, a medical device comprises a device body comprising a first section and at least one second section, wherein, in a deployed configuration of the structure: the first section defines a plurality of first loops forming a three-dimensional non-helical structure configured to anchor the device body in vasculature of a patient, each second section defines a plurality of secondary loops forming a three-dimensional non-helical structure, and each second section has a maximum cross-sectional dimension that is smaller than a maximum cross-sectional dimension of the first section Clause 2: In some examples of the medical device of clause 1, the device body comprises a plurality of second sections.

Clause 3: In some examples of the medical device of clause 1 or clause 2, the device body comprises a coil comprising a plurality of windings.

Clause 4: In some examples of the medical device of any of clauses 1-3, the maximum cross-sectional dimension of the first section is from about 10% to about 50% larger than the maximum cross-sectional dimension of each second section.

Clause 5: In some examples of the medical device of any of clauses 1-4, the device body is configured for a nominal vessel size, wherein the maximum cross-sectional dimension of the first section is about 1.1 to about 2.0 times larger than the nominal vessel size, and wherein the nominal vessel size is about 1.0 to about 1.1 times larger than the maximum cross-sectional dimension of each second section.

Clause 6: In some examples of the medical device of any of clauses 1-5, the three-dimensional non-helical structure of the first section and the three-dimensional non-helical structure of each of the one or more second sections is approximately polyhedral.

Clause 7: In some examples of the medical device of any of clauses 1-6, the device body further comprises a third section connected to the first section, wherein in the deployed configuration, the third section defines a plurality of third loops forming a helical structure configured to anchor the device body in the vasculature of the patient.

Clause 8: In some examples of the medical device of clause 7, the helical structure has a tapered configuration.

Clause 9: In some examples of the medical device of clause 8, the tapered configuration increases in diameter toward the first section.

Clause 10: In some examples, an assembly comprises a catheter defining an inner lumen; and the medical device of claim 1 positioned within the inner lumen in a delivery configuration, wherein the medical device is configured to expand from the delivery configuration to the deployed configuration in response to being deployed from the inner lumen of the catheter.

Clause 11: In some examples of the assembly of clause 10, in the delivery configuration of the medical device, the device body comprises a substantially linear configuration within the inner lumen.

Clause 12: In some examples of the assembly of clause 10 or clause 11, each of the one or more second sections trails the first section.

Clause 13: In some examples, a method comprises introducing a catheter into vasculature of a patient; delivering a medical device through the catheter to a site within the vasculature of the patient, the medical device comprising a device body comprising a first section and one or more second sections; and deploying the medical device at the site, wherein in a deployed configuration of the device body: the first section defines a plurality of first loops forming a three-dimensional non-helical structure configured to anchor the device body in vasculature of a patient, each second section defines a plurality of secondary loops forming a three-dimensional non-helical structure, and each second section has a maximum cross-sectional dimension that is smaller than a maximum cross-sectional dimension of the first section.

Clause 14: In some examples of the method of clause 13, the medical device comprises a plurality of second sections.

Clause 15: In some examples of the method of clause 13 or clause 14, the device body comprises a coil comprising a plurality of windings.

Clause 16: In some examples of the method of any of clauses 13-15, the maximum cross-sectional dimension of the first section is from about 10% to about 100% larger than the maximum cross-sectional dimension of each second section.

Clause 17: In some examples of the method of any of clauses 13-16, the device body further comprises a third section connected to the first section on an opposite of the first section from the one or more second sections, wherein in the deployed configuration, the third section defines a plurality of third loops forming a helical structure configured to anchor the device body in the vasculature of the patient.

Clause 18: In some examples of the method of clause 17, the helical structure has a tapered configuration increasing in diameter toward the first section.

Clause 19: In some examples of the method of any of clauses 13-18, deploying the medical device at the site comprises deploying the medical device such that the first section is proximal to the one or more second sections.

Clause 20: In some examples of the method of any of clauses 13-19, deploying the medical device at the site comprises deploying the medical device such that the first section is distal to the one or more second sections.

Clause 21: In some examples, a medical device comprises a device body comprising a coil comprising a first section, two or more second sections connected to one end of the first section, and a third section connected to the other end of the first section. In a primary configuration of the device body, the coil has a longitudinally extending configuration, and in a deployed configuration of the device body, the first section defines a plurality of first loops forming a three-dimensional non-helical structure configured to anchor the device body in vasculature of a patient, each second section defining a plurality of secondary loops forming a three-dimensional non-helical structure, each second section has a maximum cross-sectional dimension that is smaller than a maximum cross-sectional dimension of the first section, and the third section defines a plurality of third loops forming a helical structure configured to anchor the device body in the vasculature of the patient.

Clause 22: In some examples of the medical device of clause 21, the maximum cross-sectional dimension of the first section is from about 10% to about 100% larger than the maximum cross-sectional dimension of each second section.

Clause 23: In some examples of the medical device of clause 21 or clause 22, the device body is configured for a corresponding nominal vessel size, wherein the maximum cross-sectional dimension of the first section is about 1.1 to about 2.0 times larger than the nominal vessel size, and wherein the nominal vessel size is about 1.0 to about 1.1 times larger than the maximum cross-sectional dimension of each second section.

Clause 24: In some examples of the medical device of any of clauses 21-23, the three-dimensional non-helical structure of the first section and the three-dimensional non-helical structure of each of the second sections is approximately polyhedral.

Clause 25: In some examples of the medical device of any of clauses 21-24, each of the second sections trails the first section.

Clause 26: In some examples of the medical device of any of clauses 21-25, the helical structure of the third section has a tapered configuration.

Clause 27: In some examples, a method of forming a medical device comprises attaching a first end of an elongated structure to a mandrel; forming a first section of a device body, wherein forming the first section comprises wrapping the elongated structure about the mandrel to form a plurality of first loops forming a respective three-dimensional non-helical structure; and forming a plurality of second sections of the device body, wherein forming the plurality of second sections comprises, for each second section, wrapping the elongated structure about the mandrel to form a plurality of secondary loops forming a respective three-dimensional non-helical structure, wherein each of the second sections has a maximum cross-sectional dimension that is smaller than a maximum cross-sectional dimension of the first section.

Clause 28: In some examples of the method of clause 27, the elongated structure comprises a coil comprising a plurality of windings, and wherein wrapping the elongated structure about mandrel comprises wrapping the coil about the mandrel.

Clause 29: In some examples of the method of clause 27 or clause 28, wrapping the elongated structure comprises rotating the mandrel.

Clause 30: In some examples of the method of any of clauses 27-29, the method further comprises heating the mandrel and the elongated structure wrapped around the mandrel.

Clause 31: In some examples of the method of clause 30, the method further comprises removing the elongated structure from the mandrel.

Clause 32: In some examples of the method of any of clauses 27-31, the method further comprises forming a third section of the device body, wherein forming the third section comprises wrapping the elongated structure about the mandrel to form a plurality of third loops forming a tapered helical structure.

Clause 33: In some examples of the method of any of clauses 27-32, the maximum cross-sectional dimension of each second section is an outer diameter of each respective second section and the maximum cross-sectional dimension of the first section is an outer diameter of the first section.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
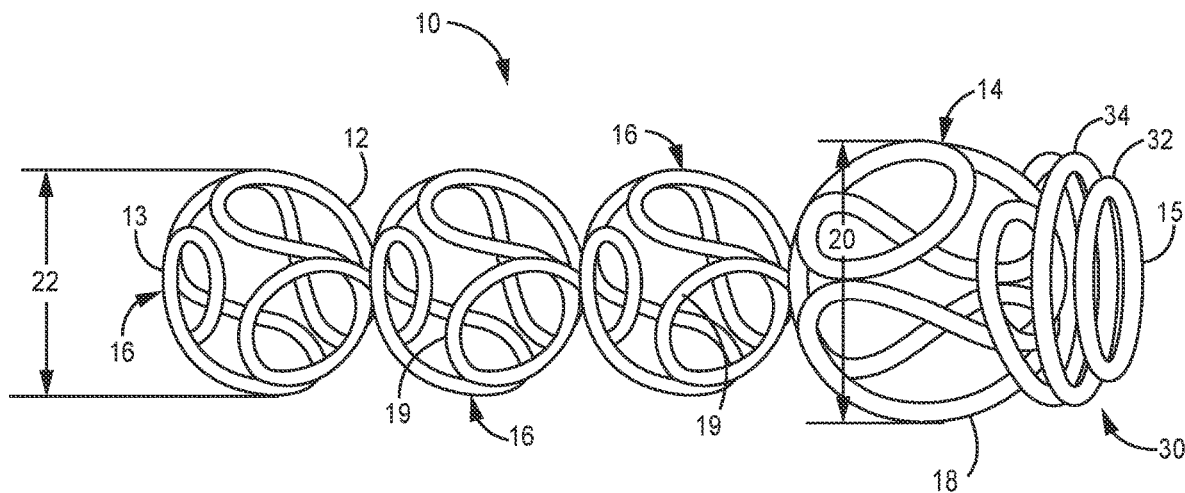
FIG. 1 is a side view illustrating an example embolization device.

This disclosure describes an implantable embolization device configured for embolizing a site within the vasculature of a patient or for use in another hollow anatomical structure of a patient. For example, the embolization device may be configured to pack a vascular site (e.g., a blood vessel) in a patient, thereby reducing blood flow at the vascular site. The embolization device can be used to, for example, occlude a blood vessel (e.g., a peripheral vessel) and sacrifice the blood vessel. The embolization device may also be referred to as embolic coils, occlusive coils, and/or vaso-occlusive coils. While a blood vessel is primarily referred to herein, the example embolization devices described herein may be used in other hollow anatomical structures or other vascular sites, such as, but not limited to, a splenic artery, a hepatic artery, an iliac artery a gastroduodenal artery, a peripheral aneurysm, an ovarian vein, or a spermatic vein.

The embolization devices described herein each have an elongated primary structure such as, for example, a linear wire or a coiled wire. The primary structure may also be referred to herein as the primary shape, a primary configuration, or a delivery configuration. Once deployed at the vascular site, the embolization device takes on a secondary configuration or shape, also referred to herein as a deployed configuration or a deployed shape. In the deployed configuration, the device includes at least two different sections that each define a three-dimensional ("3D") non-helical structure. The 3D non-helical structure defines a relatively complex 3D shape, such as loops in various orientations relative to each other, the loops having the same or different sizes, and does not define a simple helix. The orientation of the loops of the complex 3D non-helical structure can be, for example, polyhedral, such as a tetrahedron, a hexahedron, an octahedron, or the like. The incorporation of multiple 3D non-helical structures may provide added features or benefits when compared with an embolization device without multiple 3D non-helical structures. As an example, an embolization device with multiple 3D non-helical structures, may include some such structures that are configured to anchor the device at a vascular site and other structures that are configured to pack in and more completely block the site.

A catheter delivery system is often used to place an implantable embolization device at a vascular site within a patient. A delivery system can sometimes include, for example, a microcatheter configured to be delivered to the target vascular site over a guidewire, and a positioning element (e.g., a push member, optionally with a detachment mechanism that connects to the coil) that advances one or more coils out of a lumen of the microcatheter to the vascular site. Once positioned, the coil(s) are detached from the delivery system. The coil(s) may be configured to pack (e.g., fill or otherwise occupy a space through which blood flows) the vascular site thereby reducing blood flow, promoting clotting, and eventually occluding the vessel. Different types of coils can be implanted including, for example, framing or anchoring coils and packing coils.

In many cases an embolization device may exhibit different shapes depending upon its surrounding environment. The different shapes can in some cases include a primary shape as an embolization device is delivered through the narrow confines of a catheter, and a secondary shape once deployed at a vasculature site. As an example, an embolization device may have a longitudinally extending shape as it is advanced through a catheter. Upon exiting the catheter, the device may take on a secondary shape (e.g., defining a greater cross-sectional dimension than the primary shape) within the vasculature. For example, the embolization device may exhibit a secondary shape designed to more completely pack the cross-section of the vascular site.

In some examples a first section of an embolization device and one or more second sections of the device each have a deployed configuration that defines a 3D non-helical structure formed from multiple loops of the elongated primary structure of the device. The deployed configuration of the first section is configured to anchor the embolization device in vasculature of the patient, while the deployed configurations of the one or more second sections are configured to block the vessel lumen. The loops forming the first section may in some cases be referred to as anchoring loops and may be slightly larger than the nominal vessel size for which the embolization device is designed. The first section may also be helpful in anchoring the embolization device within more elastic vessels, such as some veins, that may expand to a relatively large size. The first section may additionally be helpful in compensating for sizing errors from clinicians underestimating the sizing of the target vasculature.

The deployed configurations of the second sections may have a maximum cross-sectional dimension (e.g., a diameter or width) that is smaller than the maximum cross-sectional dimension of the deployed configuration of the first section. For example, 3D non-helical structures of the second sections may be formed from loops, in some cases referred to as packing loops, that are designed to more easily pack in the space created at the embolization site by an anchoring 3D structure. For example, the second section may be deployed at least partially (e.g., partially or fully) within the first section. Each second section is configured to deploy into a smaller volume than the first section. The deployed volume of the first section or the second section may be a function of the respective maximum cross-sectional dimension.

In some examples, the embolization devices as described herein may include a third section that is different from the first and second sections. The third section has a deployed configuration that includes multiple loops of the elongated primary structure, which may be, for example, a wire or a longitudinally extending coil (the coil itself being defined by an elongated structure formed to define a plurality of turns, e.g., winding around a central axis). The multiple loops of the third section may be helical in nature. In some examples one or more of the helical loops may have a maximum cross-sectional dimension that is slightly larger than the nominal vessel size for which the device is designed. In some examples the diameter of one or more helical loops may be approximately the same as the maximum cross-sectional dimension of the deployed configuration of the first section(s). Accordingly, the deployed configuration of the third section may be configured to provide additional anchoring of the embolization device within the patient's vasculature. In some examples, one or more of the helical loops of the third section may have a maximal cross-sectional dimension that is smaller than the nominal vessel size for which the device is designed. Accordingly, the deployed configuration of the third section may be configured to help ensure that these loops of the coil assume a deployed configuration, rather than an elongated configuration, upon exiting the delivery system. In some examples some or all of the loops of the third section may have a tapered configuration, in which the loops' diameters increase from one end toward the other end.

The third section of the device may be closest to the first section, and opposite the first section from the second sections. Accordingly, the order of the sections may extend from the third section at a leading end to the first section to the second sections at a trailing end. The leading end can be, for example, a distal end in some examples or a proximal end in other examples, and the trailing end can be, for example, a proximal end in some examples and a distal end in other examples.

When performing some vasculature embolization medical procedures, two objectives are to position an embolization device without displacement and to quickly and fully block the vessel lumen. The rate of blood flow in vessels, which can be very high in some arteries, for example, can make positioning an embolization device and occluding a vessel quite challenging, especially when compared with embolizing a space with lower flow drag forces such as, for example, an aneurysm. Example embolization devices as described herein have deployed configurations with multiple 3D non-helical structures that may be configured to address these concerns by providing a first section that anchors the embolization device in a blood vessel and one or more second sections that are configured to pack a scaffold defined by the first section. Decoupling the anchoring and packing functions of the embolization in this manner may help achieve more effective outcomes.

The embolization devices described herein may also be useful for aneurysm occlusion. In these examples, the first section can be configured to provide apposition against an aneurysm wall and the one or more second sections can be configured to pack the aneurysm sac.

As described herein, example embolization devices have a primary structure that may also be referred to as a primary shape, a primary configuration, or a delivery configuration. Example embolization devices further have a secondary configuration when deployed at a vascular site, which may also be referred to as a secondary structure or shape or a deployed configuration, shape or structure. Further, example embolization devices are described as including one or more first sections, one or more second sections (e.g., two or more second sections), and in some examples a third section. As described herein, each of these sections of an example device has its own primary configuration and secondary, e.g., deployed, configuration. These structures can alternatively be described as respective sections of a device's overall primary configuration and deployed configuration. Thus, a 3D non-helical structure may be described herein as part of the deployed configuration of the first section of an example embolization device and may alternatively be referred to as a first section of the deployed configuration of an example embolization device. For convenience, such structures may also be referred to herein as a first, second, and third deployed configurations or structures, respectively, each referring to the respective section of the device's overall deployed configuration.

FIG. 1 is a side view illustrating example implantable embolization device 10 configured to embolize a site in the vasculature of a patient. FIG. 1 depicts embolization device 10 in a secondary (or deployed) configuration that includes multiple 3D non-helical structures, which in some cases may also be referred to as complex shapes, configurations, or structures. The secondary configuration shown in FIG. 1 may represent the configuration of device 10 in its relaxed state with no external forces being applied to device 10. In some cases, the material from which device 10 is formed may not be self-supporting, such that device 10 may flatten under its own weight.

Embolization device 10 includes a device body 12 that is shaped to produce the deployed configuration illustrated in FIG. 1. In some examples, device body 12 may be a wire or other filamentous material. In some examples, device body 12 may be a length of coiled material. For example, device body 12 may be a length of coil formed from many windings or turns of a wire or other suitable material. In some examples, device body 12 may also incorporate other elements previously disclosed to assist in the function of a detachable coil, such as detachment elements and stretch-resistant elements.

Figure 2:
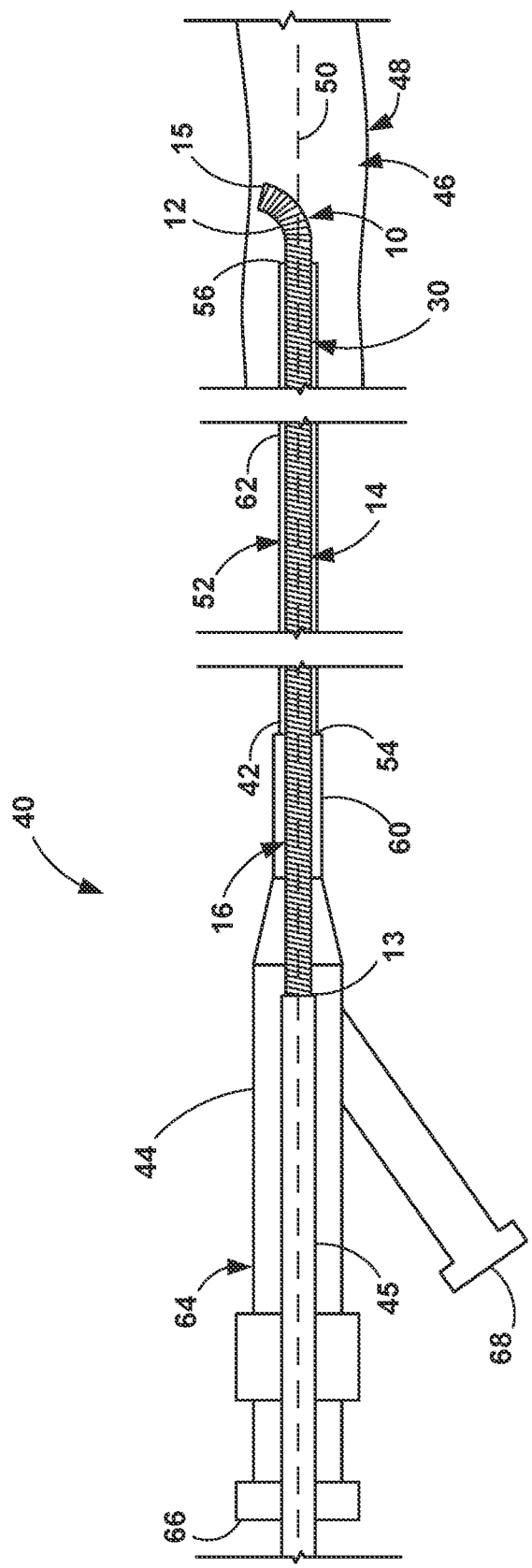
FIG. 2 is a schematic diagram illustrating an example assembly including a catheter system for delivering the example embolization device of FIG. 1 to a vascular site.

Referring to FIG. 2, embolization device 10 also has a primary configuration (also referred to as a delivery configuration), e.g., shape or structure, not depicted in FIG. 1. As illustrated in FIG. 2, device body 12 of embolization device 10 has a primary shape that is configured to fit within inner lumen 42 of catheter 44 for delivering device 10 to a target vasculature site 46. In such cases the primary shape may be, for example, a longitudinal or lengthwise extension of device body 12. As partially shown in the example of FIG. 2, device body 12 is a length of coil extending from trailing end 13 to lead end 15. In some examples, the coil has a primary configuration that is a substantially linear configuration within inner lumen 42 of catheter 44. As device 10 is deployed from inner lumen 42 at a vascular site 46, device body 12 exits catheter 44 and assumes its second configuration (e.g., shown in FIGS. 1 and 3). When formed from a coil, device body 12 may be referred to as a "primary coil" to differentiate the structure and configuration of device body 12 from other "secondary" loops and bends of the coil itself in a secondary configuration of the embolization devices described herein.

Returning to FIG. 1, embolization device 10 includes first section 14 and one or more second sections 16. Although three second sections 16 are shown in FIG. 1, in other examples, embolization device 10 can include any suitable number of second sections 16, such as one, two, or more than three second sections 16 trailing first section 14.

In the deployed configuration of FIG. 1, each of the first and second sections 14, 16 include multiple loops 18 of device body 12 that form a separate 3D non-helical structure for each of the sections 14, 16. Loops 18 forming first section 14 may be described as first loops herein, while loops 19 forming each second section 16 may be described as secondary loops. In some examples, the 3D non-helical structure of first section 14 is configured to anchor the device 10 in vasculature of a patient and the 3D non-helical structures of second sections 16 are configured to pack a vascular site (e.g., a vessel lumen or an aneurysm sac) to occlude or embolize the vascular site. Accordingly, in some cases the loops forming the deployed structure of first section 14 may be referred to as "anchoring" loops and the loops forming the deployed structure of second sections 16 may be referred to as "packing" or "filling" loops. As an example, the deployed first section 14 may define scaffolding and the one or more second sections 16 may be configured to fit within and pack the scaffolding, such that the one or more second sections 16 tuck into first section 14. An example of this configuration is shown and described with respect to FIG. 13.

First section 14 has a maximum cross-sectional dimension 20 and each second section 16 has a maximum cross-sectional dimension 22. Maximum cross-sectional dimension 22 of each second section 16 is smaller than maximum cross-sectional dimension 20 of first section 14. As a result, each second section 16 is configured to deploy into a smaller volume than first section 14. The maximum cross-sectional dimensions of embolization devices, first sections, second sections, and third sections described herein refer to the dimension of the overall structure (e.g., from edge to edge along a plane), rather than the cross-sectional dimension of the wire, coil, or other elongated structure that is used to form the respective structure.

The use of deployed second sections 16 with a smaller maximum cross-sectional dimension (e.g., a smaller deployed volume) than first section 14 may facilitate packing of the vasculature site (e.g., an aneurysm sac or a parent blood vessel). In some examples, first section 14 forms a scaffold within the vessel lumen or aneurysm sac as it anchors to the vessel walls at the site. Smaller maximum cross-sectional dimension 22 of each second section 16 may assist the loops forming the second sections 16 in packing the scaffolding provided by the first section 14. In some examples, maximum cross-sectional dimension 20 of first section 14 is from about 10% to about 100% larger than maximum cross-sectional dimension 22 of each second section 16, such as about 10% to 50% larger. When used to modify a numerical value, the term "about" is used herein may refer to the particular numerical value or nearly the value to the extent permitted by manufacturing tolerances. As an example, "about 10%" means "10% or nearly 10% to the extent permitted by manufacturing tolerances."

In some cases, as discussed below, maximum cross-sectional dimension 20 of first section 14 is selected based on the size of the vessel in which device 10 is intended to be used, and the size of maximum cross-sectional dimension 22 of each second section 16 is selected based on the determined maximum cross-sectional dimension 20 of first section 14. For example, maximum cross-sectional dimension 22 of each second section 16 may be selected to sit inside the larger size of maximum cross-sectional dimension 20 of first section 14 when device 10 is deployed at a vascular site in a patient.

In some examples, embolization devices may be configured or designed to be used with blood vessels of a particular size. Thus, in some cases, a clinician may evaluate the size of vessel to be embolized and then select a specific embolization device 10 configured for that particular size from among multiple embolization devices as described herein, with the devices varying in size according to a range of nominal vessel sizes. In some examples, embolization device 10 may be configured for a particular nominal vessel size. In such examples, maximum cross-sectional dimension 20 may be slightly larger than the nominal vessel size. For example, maximum cross-sectional dimension 20 may be about 1.1 to about 2 times (exactly 1.1 to 2 or within 10%) larger than the nominal vessel size, such as about 1.1 to about 1.4 times larger than the nominal vessel size or about 1.1 to about 1.3 times larger than the nominal vessel size. Too large of a maximum cross-sectional dimension 20, such as larger than about 2 times larger than the nominal vessel size in some examples, may adversely impact the ability of the device 10 to form a loop within the vasculature when device 10 is deployed in the vasculature.

In some examples the maximum cross-sectional dimensions of second sections 16 may be approximately the same (e.g., the same but for manufacturing tolerances) for each second section 16, or the dimensions may vary between one second section 16 and another second section 16. In examples in which the maximum cross-sectional dimensions 22 are different due to, e.g., design and/or tolerances, each maximum cross-sectional dimension 22 is still smaller than maximum cross-sectional dimension 20 of first section 14. In some examples, embolization device 10 is configured for a nominal vessel size and maximum cross-sectional dimension 22 is equal to or slightly smaller than the nominal vessel size. For example, maximum cross-sectional dimension 22 may be about 85% to about 100% of the nominal vessel size, or the nominal vessel size may be about 1.0 to about 1.1 times larger (e.g., exactly 1.0 to 1.1 or within 10%) than maximum cross-sectional dimension 22.

As described herein, example implantable embolization devices have a secondary or deployed configuration that includes multiple 3D non-helical structures. As illustrated in FIG. 1, embolization device 10 includes first section 14 with a 3D non-helical structure, and three second sections 16, each having a 3D non-helical structure. In some cases, 3D non-helical structures may also be referred to as complex shapes or configurations because the structures are formed from one or more loops positioned in various planes, unlike, e.g., a simpler structure such as a helical coil. In some examples first section 14 and/or second sections 16 may include a 3D non-helical structure that is approximately polyhedral in that each loop of the structure approximates one of the faces of a polyhedron. In the example of FIG. 1, each of the 3D non-helical structures is formed from six loops that approximate the six face planes of a cube. In some examples a 3D non-helical structure may be cubic, tetrahedral, octahedral or configured as any solid with sides shaped as a regular polygon.

In some examples, including some of those described herein, a 3D non-helical structure may be considered to approximate a sphere to a greater or lesser extent. In such cases the maximum cross-sectional dimension of each second section is an outer diameter of the second section. Further, the maximum cross-sectional dimension of a first section is an outer diameter of the first section. For example, the 3D non-helical structures exhibited by embolization device 10 shown in FIG. 1 can be considered approximately spherical such that maximum cross-sectional dimension 20 may be considered an outer or outside diameter 20 of first section 14. In a similar manner, maximum cross-sectional dimension 22 may be considered an outer diameter 22 of second sections 16.

The example embolization devices described herein include multiple sections with three-dimensional non-helical structures when deployed at a vascular site. The multiple sections may include at least one (e.g., one or more) first section 14 and at least one (e.g., one or more) second sections 16 that are smaller than the first section(s). Some example embolization devices may include two or more second sections that are connected to an adjacent first section. As shown in FIG. 1, the deployed configuration of example device 10 includes three adjacent second sections 16 that are connected to one first section 14. More or less than three adjacent second sections 16 may be included in some example embolization devices.

In some examples, embolization device 10 further includes third section 30 that is configured to anchor embolization device 10 in the patient's vasculature. As an example, third section 30 may be configured to anchor embolization device 10 along with the first deployed structure of first section 14. In the deployed configuration shown in FIG. 1, third section 30 includes multiple loops, also referred to herein as a plurality of third loops. In the example of FIG. 1, third section 30 is connected to first section 14 and is positioned on an opposite side of first section 14 from second sections 16. In some examples, the third loops forming third section 30 form a helical structure, e.g., a spiral structure, configured to anchor device 10 in the patient's vasculature. In some examples, the helical structure has a tapered configuration that increases in diameter from a leading loop 32 toward a trailing loop 34 connected to first section 14, as shown in FIG. 1. Alternatively, the helical structure of third section 30 may increase in diameter from trailing loop 34 towards leading loop 32. In examples in which third section 30 has a tapered helical configuration, third section 30 may define a conical spiral, e.g., a three-dimensional spiral that extends along the outer surface of an imaginary cone. The spiral may taper in a leading direction (away from second sections 16) in some examples, as shown in FIG. 1, or may taper in a proximal direction in other examples. In some examples, the smallest loop of the spiral is smaller than the intended vessel treatment range of the device so that this section of the coil is assured to assume a deployed configuration, rather than an elongated configuration, when exiting the delivery system and deploying into the vasculature.

The loops of third section 30 may not be closed loops, in which the loops of the coil are coplanar and a loop of a coil touches an adjacent loop in the "at rest" state (in which no compressive forces are applied to third section 30 from a catheter, a blood vessel, or the like). Spacing the loops from each other in a longitudinal direction (e.g., proximal to distal direction or distal to proximal direction) may provide the loops with room to bend relative to each other and enable larger loops to decrease in cross-sectional dimension by spreading longitudinally when anchoring in a relatively small diameter vessel. In some examples, in its at rest secondary configuration, in which no outward forces are being applied to device 10 from a vessel wall or a catheter, the loops 32, 34 (and other loops, if present) may be separated from each other. In addition, in examples in which loops 32, 34 (and other loops, if present) have different maximum (or greatest) cross-sectional dimensions (e.g., diameters) from each other, each loop of third section 30 may differ in a maximum cross-sectional dimension from an adjacent loop by a predetermined amount. For example, if third section 30 is defined by an elongated structure having a diameter of 0.25 mm, each loop may be 0.50 mm larger in diameter than an immediately distal (or proximal in some examples) loop. Other loop sizes may also be used in other examples.

In examples in which third section 30 is closer to a leading end of device 10 than first section 14 (e.g., a distal-most section of embolization device 10 or a proximal-most section of embolization device in other examples), third section 30 may be deployed from catheter 44 before first section 14 and second sections 16. For example, the first loop 32 of third section 30 may engage with the vessel wall and then subsequent loops of third section 30 may deform into a helix against the vessel wall, thereby potentially changing the shape of third section 30, e.g., from a conical spiral to a helix having more uniform loop sizes. The helical structure of third section 30 may enable third section 30 to engage the vessel wall at distal end 56 of catheter 44 (FIG. 2) and anchor at the target vascular site as embolization device 10 is deployed from catheter 44. For example, third section 30 may be configured to engage the vessel wall in a relatively straight (e.g., cylindrical) vessel segment.

While first section 14 is also configured to engage the vessel wall to anchor embolization device 10 within the vasculature, the configuration (e.g., helical structure) of third section 30 may enable third section 30 to be deployed more effectively than first section 14, which has smaller individual loops though a similar overall deployed outer diameter, thereby enabling embolization device 10 to more effectively anchor within the blood vessel as embolization device 10 is deployed from catheter 44. The more effective anchoring of embolization device 10 may enable embolization device 10 to begin packing at or relatively close to distal end 56 of catheter 44, rather than sliding along the vessel wall without engaging the vessel wall. The structure of embolization device 10 that enables it to begin packing at or relatively close to distal end 56 of catheter 44 (or other deployment location of a catheter) may provide a clinician with more precise control of the implant position of embolization device 10 in the vasculature of the patient, which may provide better treatment outcomes (e.g., in sacrificing the blood vessel via device 10).

In some examples, the third loops forming the helical structure of third section 30 may further assist in anchoring device 10 because the third loops may be configured to exert a larger radial force against the vessel wall compared to first section 14 and/or second sections 16. For example, helical loops may assist in penetrating the open space inside the vessel. Further, in examples in which third section 30 includes tapering loops, the various loop sizes defined by third section 30 may enable third section 30 to expand (as it is deployed from the catheter) to accommodate various vessel sizes (in cross-section). In these examples, embolization device 10 may be configured to accommodate clinician sizing preference (e.g., some clinicians may prefer a larger distal loop or a smaller distal loop based on their personal experience implanting embolization devices in patients), as well as vessel sizing uncertainty when selecting a particular size of embolization device 10 to implant in a patient. In some cases, embolization device manufacturers may provide embolization devices in 1 millimeter increments corresponding to different vessel sizes (in cross-section), e.g., 4 mm vessels, 5 mm vessels, and the like. In contrast to these devices configured for a specific vessel size, embolization device 10 that is configured to accommodate a range of vessel sizes may better enable a clinician to select a device 10 that may provide a positive outcome for the patient by requiring a less accurate determination of the patient's vessel size.

In some examples, the first 180 degrees of the smallest loop (e.g., loop 32) defined by third section 30 may be selected to define a cross-sectional size that is the same size or smaller than (e.g., within 10%) the cross-sectional size (e.g., diameter) of the smallest vessel a clinician may treat with embolization device 10. In addition, in addition to or instead of the aforementioned parameter, in some examples, the cross-sectional size of the largest loop (e.g., loop 34) defined by third section 30 may be selected to have a cross-sectional size that is larger than (e.g., 10% to 50% larger, such as 25% to 30% larger) the largest vessel a clinician may treat with embolization device 10. By oversizing the largest loop, third section 30 may provide enough radially outward force to engage with the vessel wall and help anchor device 10 to the vessel wall.

In some examples, such as examples in which third section 30 defines a conical spiral, third section 30 may also help to center embolization device 10 within a vessel wall, which may enable embolization device 10 to achieve a higher packing density in some cases. A higher packing density may provide more effective at stopping of blood flow through the blood vessel within a given amount of time by providing a larger kinetic energy sink for the blood flow.

Third section 30 may be formed from any suitable material. In some examples, third section 30 is formed from a different material (e.g., chemical composition) than first section 14 and/or second sections 16. In other examples, third section 30 is formed from the same material as first section 14 and/or second sections 16. For example, third section 30 may be integrally formed with first and second sections 14, 16, and may be formed from the same material as first and second sections 14, 16. In any of these examples, third section 30 may be formed from a metal alloy, such as platinum tungsten (e.g., approximately 98% Pt and approximately 2% Tungsten), platinum, iridium, or other suitable biocompatible materials. In addition, in some examples, third section 30 may be at least partially formed from a material that enables third section 30 to engage with the vessel wall (e.g., by friction fit or using an adhesive material) for a relatively short period of time that is less than the intended implant time of embolization device 10.

For example, at least part of an outer surface of third section 30 may be at least partially formed from a biodegradable and biocompatible hydrophilic material, such as, but not limited to poly(lactic-co-glycolic acid) (PGLA), where the biodegradable and biocompatible hydrophilic material is configured to be desiccated (dehydrated) as a result of sterilization of embolization device 10. For example, third section 30 may be formed from a metal or fiber enlaced with or coated with PGLA or other biodegradable and biocompatible material. The PGLA or other biodegradable and biocompatible material can, for example, be formed as fibers that are enlaced with other fibers of the structure forming third section 30. The state in which the biodegradable and biocompatible material of third section 30 is dehydrated may also be referred to as a dehydrated state of third section 30.

In its dehydrated state, third section 30 may be configured to better stick to (e.g., by static friction) and engage with the vessel wall compared to its non-dehydrated (i.e., hydrated) state. This may due to, for example, the surface features that are more prevalent in its dehydrated state compared to the hydrated state. After embolization device 10 is implanted in the blood vessel, the moisture in the blood may hydrate the material of third section 30, e.g., until the material reaches equilibrium with its environment. In its hydrated state, third section 30 may be softer compared to the dehydrated state, and may soften and engage less with the vessel wall, e.g., due to changes in the surface features, which may become less prevalent in the hydrated state. However, because embolization device 10 may be fully deployed at this point, first section 14 may provide further aid in anchoring device 10 in the blood vessel. In this way, the material of third section 30 may be used to further aid in more accurate deployment of embolization device 10 by anchoring device 10 proximate distal end 56 of catheter 44 to enable device 10 to pack at or relatively close to the catheter tip.

In other examples, embolization device 10 includes first section 14 and one or more second sections 16, but does not include third section 30.

FIG. 2 is a schematic diagram illustrating example assembly 40, which includes embolization device 10 positioned within inner lumen 42 of catheter 44. FIG. 2 is a schematic cross-sectional view of catheter 44, where the cross-section is taken along longitudinal axis 50 of catheter 44. Longitudinal axis 50 may be a central longitudinal axis of one or more components of catheter 44, such as elongated body 52 of catheter 44. Elongated body 52 of catheter 44 extends from proximal end 54 to distal end 56. In some examples, catheter 44 may include strain relief member 60. In such examples, proximal end 54 of elongated body 52 may be partially covered by strain relief member 60, such that proximal end 54 of elongated body 52 may be more proximal than as shown in FIG. 2.

Elongated body 52 has an outer wall 62 that defines lumen 42. In some examples, elongated body 52 may define one or more additional lumens (not shown) in addition to lumen 42. Such additional lumens may be used to aspirate fluid and/or deliver a drug or medical agent to a vessel. In some examples, catheter 44 may further include a hub 64 positioned at proximal end 54 of elongated body 52. In such examples, lumen 42 may extend longitudinally through elongated body 52 to hub 64. Hub 64 may include at least one of a first port 66 or a second port 68, one or both of which may be in fluid communication with lumen 42.

Catheter 44 is configured to be navigated through vasculature of a patient to deliver embolization device 10 to target site 46 within the patient's vasculature. FIG. 2 depicts an example in which site 46 is within a blood vessel 48 of a patient. Some example assemblies may also include a positioning device 45, which may also be referred to as positioner 45 or a pushing member. Positioner 45 is configured to advance embolization device 10 through inner lumen 42 of catheter 44 in order to deploy device 10 at site 46. In some examples positioning device 45 may also positively attach to embolization device 10, and then detach from device 10 once it has been deployed at site 46. A variety of positioning devices or positioners may be used to deliver example embolization devices described herein, including those described in U.S. Pat. No. 8,328,860, entitled, "IMPLANT INCLUDING A COIL AND A STRETCH-RESISTANT MEMBER," the disclosure of which is hereby incorporated herein by reference in its entirety.

As discussed with respect to FIG. 1, example embolization devices have a primary configuration designed to fit within a catheter lumen. As shown in FIG. 2, in some examples, device body 12 is formed from a coil that extends from trailing end 13 to leading end 15. The coil has a substantially linear configuration within inner lumen 42 of catheter 44 as device 10 is configured to be advanced through inner lumen 42 during deployment of device 10 at target site 46 within blood vessel 48. The coil exits inner lumen 42 of catheter 44 and begins to assume the secondary configuration as device 10 is deployed to target site 46. FIG. 2 depicts embolization device 10 in the first or primary configuration, with the exception that the leading end 15 of device 10 has begun to assume the secondary configuration outside inner lumen 42 of catheter 44. Example embolization device 10 includes first section 14, multiple second sections 16, and third section 30, as also described with respect to FIG. 1. For clarity, multiple second sections 16 are referenced in FIG. 2 with a single instance of reference numeral 16.

Figure 3:
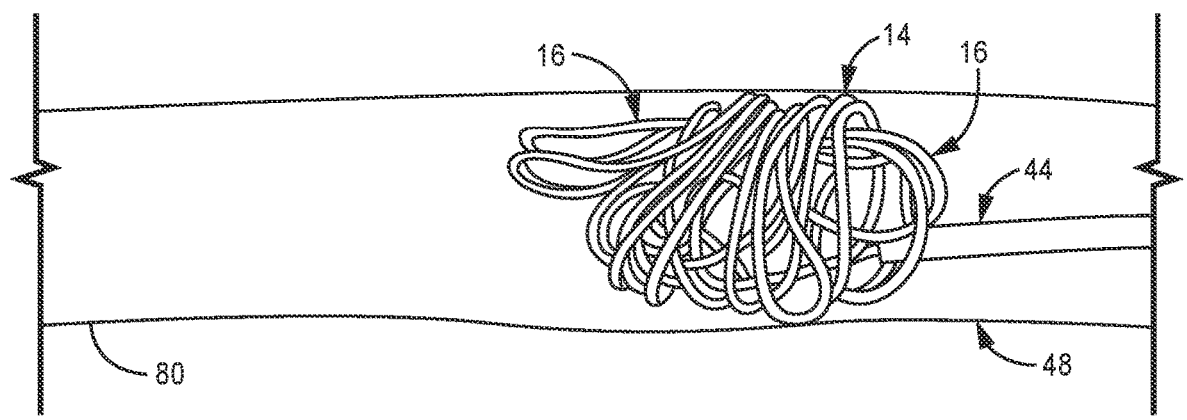
FIG. 3 is a schematic diagram illustrating the embolization device of FIG. 1 deployed at a vascular site.

In some examples the sections of example embolization devices are arranged in different manners. In FIGS. 1-3, example embolization device 10 includes one first section 14 and three second sections 16 that trail first section 14. In some cases, the second sections 16 are connected to first section 14 and may also be adjacent first section 14. Example embolization device 10 further includes third section 30 that is closer to a lead end than first section 14. In some examples, third section 30 is connected and adjacent to first section 14 as depicted in FIGS. 1-3.

As depicted in the figures, example embolization device 10 can include three second sections 16 connected to one first section 14, which is connected to a third section 30. It will be understood that the number of the sections may be changed depending on, e.g., a particular target site, delivery method, etc. For example, in some examples, more than three or fewer than three second sections may be used. In some examples the first, second and third sections may be not be connected directly or be adjacent but may have some open length of elongated structure between sections.

FIG. 3 is a schematic diagram illustrating embolization device 10 in a deployed configuration at target site 46 within blood vessel 48. Also shown in FIG. 3 is catheter 44 deploying one or more second sections 16 into a scaffold defined by first section 14. In other examples, embolization device 10 can be deployed at other vascular sites, such as within an aneurysm sac.

First section 14 includes a 3D non-helical structure configured to engage with blood vessel wall 80 and thereby anchor device 10 in blood vessel 48. The anchoring structure provided by first section 14 may be packed with the one or more second sections 16 of embolization device 10. For example, as shown in FIG. 3, first section 14 deployed within blood vessel 48 can define a scaffold (e.g., a framework including spaces) and at least part of the one or more second sections 16 can tuck into and pack the scaffold defined by first section 14 (e.g., into the spaces defined between loops or other structures of the deployed first section 14). As an example, the smaller loops defined by second section 16 may deploy within the scaffold defined by first section 14. As FIG. 3 illustrates, catheter 44 can be positioned relative to a deployed first section 14 such that subsequently deployed one or more second sections 16 are delivered within a scaffold defined by first section 14.

Configuring first section 14 to anchor within blood vessel 48 or at another vascular site may result in first section 14 being insufficient to pack the vascular site and reduce blood flow at the vascular site. The smaller deployed volume of each one or more second section 16 enables the one or more second sections 16 to fit within and pack the scaffolding defined by first section 14 to help obstruct blood vessel 48. Thus, by including one or more second sections 16 in embolization device, embolization device 10 can exhibit both effective anchoring at the vascular site and effective packing at the vascular site.

As described with respect to FIGS. 1 and 2, in some examples, embolization device 10 includes third section 30 connected to first section 14 on an opposite side of first section 14 from one or more adjacent second sections 16. In the deployed configuration of FIG. 3, third section 30 includes multiple helical loops that taper in diameter, increasing in diameter from end loop 32 (e.g., a leading loop) to beginning loop 34 (e.g., a trailing loop), which is connected, and adjacent, to first section 14. Third section 30 is configured to anchor device body 12 in the vasculature of the patient, e.g., by engaging with wall 80 of blood vessel 48 at vascular site 46.

Figure 4:
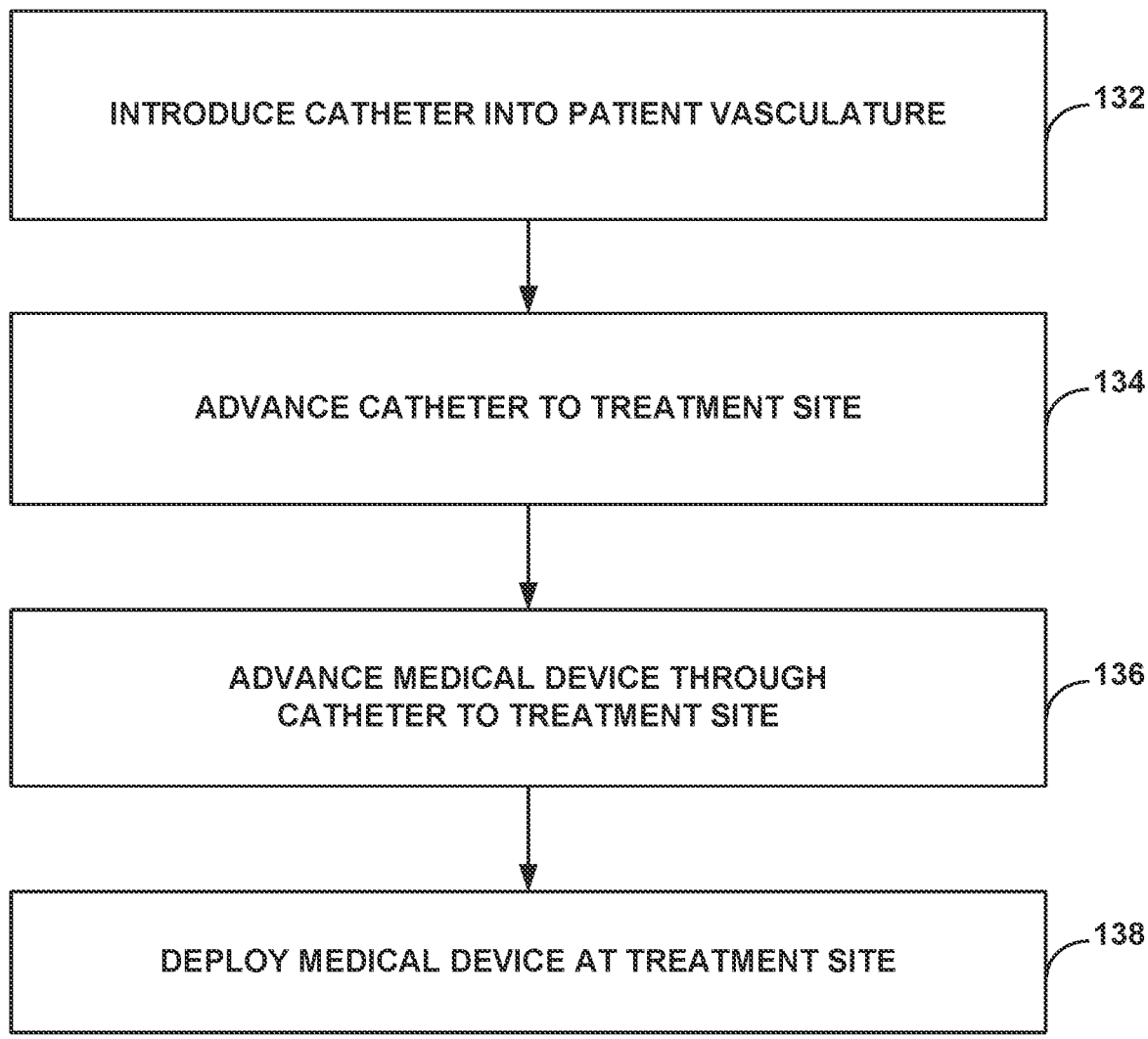
FIG. 4 is a flow diagram illustrating an example method of deploying an example embolization device.

FIG. 4 is a flow diagram illustrating an example method of deploying an example embolization device, such as the example embolization devices described herein. The method includes introducing catheter 44 into vasculature of a patient (132) and advancing catheter 44 to target site 46 (FIG. 3) within the patient's vasculature (134). Once the distal end 56 of catheter 44 is at the desired position relative to target site 46, a clinician may advance embolization device 10 through inner lumen 42 of catheter 44 (136) and deploy embolization device 10 at target site 46 (138). For example, the clinician may apply a pushing force to trailing end 13 of device body 12 (FIG. 2) using positioner 45 or another device to deploy device body 12 from inner lumen 42 and deploy embolization device 10 at target site 46.

Upon deploying embolization device 10 at the desired vascular treatment site 46, device body 12 of embolization device 10 assumes a deployed configuration, e.g., as shown in FIG. 3. In some examples, the deployed configuration includes a first section 14 that defines multiple first loops that form a 3D non-helical structure configured to anchor device body 12 at the treatment site and one or more second sections 16 that each defines multiple secondary loops that form a 3D non-helical structure. Further, in some cases each second section 16 has a maximum cross-sectional dimension that is smaller than a maximum cross-sectional dimension of first section 14.

Embolization device 10 as well as other embolization devices described herein that include first section 14 and one or more second sections 16 may be formed using any suitable technique, such as by using a mandrel that includes different rods extending therefrom to define different parts of embolization device 10.

Figure 5:
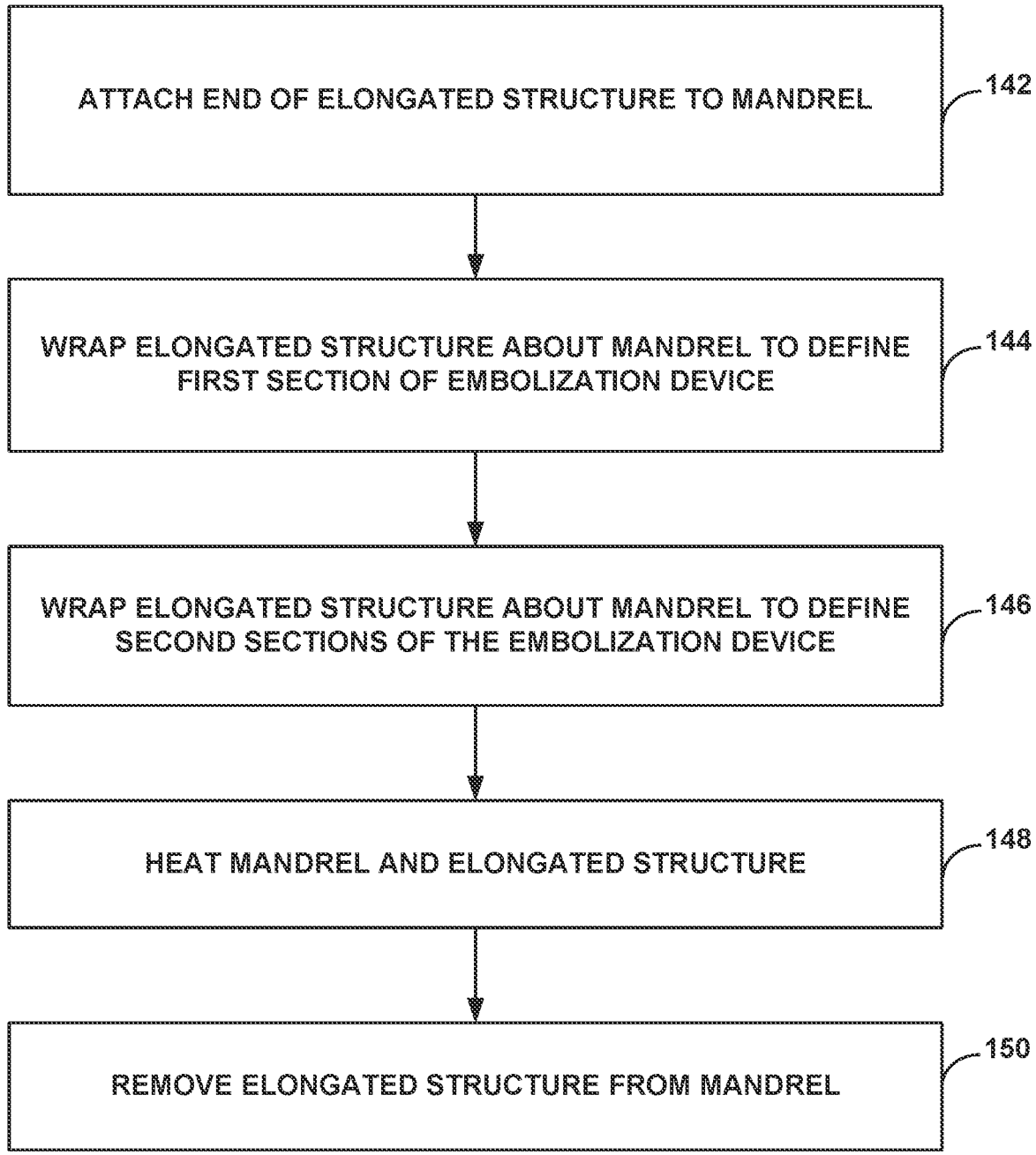
FIG. 5 is a flow diagram illustrating an example method of forming an example embolization device.

FIG. 5 is a flow diagram illustrating an example method of forming an embolization device, such as example embolization device 10 shown in FIG. 1. While FIG. 5 is described with reference to embolization device 10, in other examples, the method shown in FIG. 5 may be used to form other embolization device including a first section and one or more second sections, as described herein. In some examples, the method includes attaching an end of an elongated structure (e.g., a wire or a coil) to a mandrel (142). For example, in some cases the elongated structure may be attached to the mandrel by inserting one end of the elongated structure into a starting hole defined by the mandrel. In some cases, the elongated structure may be stretched and wound tightly around part of the mandrel to secure the end of the elongated structure relative to the mandrel.

In some examples, the elongated structure may be a metal wire in a linear configuration or a metal wire formed into a primary coil, such as in the examples shown in FIG. 2. Example embolization devices such as those described herein may be formed of any suitable, biocompatible material. In some examples, the elongated structure may be formed from a metal or metal alloy, including platinum, a platinum alloy, palladium, Nitinol, stainless steel and/or any other metal material characterized as having suitable biocompatibility.

As shown in FIG. 5, the example method also includes wrapping the elongated structure about the mandrel to define first section 14 of embolization device 10 (144). For example, the elongated structure may be wrapped around the mandrel to form multiple first loops that form a 3D non-helical structure in the deployed configuration of first section 14. The method also includes wrapping the elongated structure about the mandrel, e.g., one or more second winding cores extending from the main shaft of the mandrel, to define one or more second sections 16 of embolization device 10 (146). For example, the elongated structure may be wrapped around the mandrel to form multiple secondary loops forming a corresponding 3D non-helical structure in the deployed configuration of the second sections 16.

After wrapping the elongated structure around the mandrel, the mandrel and the elongated structure may be heated (148) and the resulting structure remove from the mandrel (150).

In some examples, the method shown in FIG. 5 also includes forming a third section of embolization device 10, such as by wrapping the elongated structure about the mandrel 90 to define form multiple third loops that are part of a tapered helical structure.

In some examples, embolization devices such as those described herein may include an elongated structure, e.g., a primary coil, that includes wires of different sizes. As an example, in some cases a primary coil may be formed with two wires of different diameters or a single wire with sections having different diameters. In some examples, a leading section of a primary coil may be formed from a wire with a larger diameter than the diameter of a wire forming a trailing section of the primary coil. In some examples, a leading section of a primary coil may be formed from a wire with a smaller diameter than the diameter of a wire forming a trailing section of the primary coil.

According to some examples, embolization devices as described herein may include one or more fibers. For example, a device may include multiple fibers, at least one bundle of fibers, or multiple fiber bundles. In some examples the fiber(s) can be enlaced, tied, or knotted to a number of places on the embolization device. In some examples the fibers or fiber bundles may be disposed so that they are not tied or knotted to the device, thereby avoiding potentially obstructive bundles that might hinder deployment of the device. In some examples one or more fibers may be nonabsorbable. Example materials that may be used include, but are not limited to, nylon, polyethylene, and/or polypropylene. In some examples, one or more fibers may be bioabsorbable. Example bioabsorbable materials that may be used include, but are not limited to, polyglycolic acid (PGA), polylactic acid (PLA), PGLA, and/or polydioxanone (PDO).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A medical device comprising:
    a device body comprising:
        a first section;
        a plurality of second sections; and
        a third section connected to the first section on an opposite side of the first section from the plurality of second sections,
    wherein the device body defines a longitudinal axis extending in a direction from the third section to the plurality of second sections, and
    wherein, in a deployed configuration of the device body:
        the first section defines a plurality of first section loops forming a three-dimensional non-helical structure configured to anchor the device body in vasculature of a patient,
        each second section of the plurality of second sections defines a plurality of second section loops forming a three-dimensional non-helical structure, the three-dimensional non-helical structure of each second section being an approximately polyhedral structure having three or more sides,
        each second section of the plurality of second sections has a maximum cross-sectional dimension that is smaller than a maximum cross-sectional dimension of the first section, and
        the third section forms a different sized and shaped structure than the three-dimensional non-helical structures formed by the first and second sections and defines a third section loop larger than at least one first section loop of the plurality of first section loops.

2. The medical device of claim 1, wherein the three-dimensional non-helical structure of the first section is the approximately polyhedral structure.

3. The medical device of claim 1, wherein the approximately polyhedral structure is approximately cubic, approximately tetrahedral, or approximately octahedral.

4. The medical device of claim 1, wherein the approximately polyhedral structure having three or more sides is defined by six loops.

5. The medical device of claim 1, wherein the plurality of second sections comprises at least three second sections.

6. The medical device of claim 1, wherein the maximum cross-sectional dimension of the first section is from about 10% to about 50% larger than the maximum cross-sectional dimension of each second section of the plurality of second sections.

7. The medical device of claim 1, wherein the device body is configured for a nominal vessel size, wherein the maximum cross-sectional dimension of the first section is about 1.1 to about 2.0 times larger than the nominal vessel size, and wherein the nominal vessel size is about 1.0 to about 1.1 times larger than the maximum cross-sectional dimension of each second section of the plurality of second sections.

8. The medical device of claim 1, wherein in the deployed configuration, the third section defines a plurality of loops forming a helical structure configured to anchor the device body in the vasculature of the patient, the plurality of loops including the third section loop.

9. The medical device of claim 8, wherein the helical structure has a tapered configuration.

10. The medical device of claim 1, wherein the device body comprises a coil comprising a plurality of windings.

11. The medical device of claim 1, wherein the third section is formed from a material having a chemical composition different from a chemical composition of a material from which at least one of the first section or the plurality of second sections are formed.

12. The medical device of claim 1, wherein the third section is configured to exert a larger radial force against a vessel wall compared to at least one of the first section or the plurality of second sections.

13. An assembly comprising:
    a catheter defining an inner lumen; and
    the medical device of claim 1 positioned within the inner lumen in a delivery configuration, wherein the medical device is configured to expand from the delivery configuration to the deployed configuration in response to being deployed from the inner lumen of the catheter.

14. A medical device comprising:
    a device body comprising a first section, two or more second sections connected to one end of the first section, and a third section connected to the other end of the first section distal to the first section, wherein, in a primary configuration of the device body, the device body has a longitudinally extending configuration, and wherein, in a deployed configuration of the device body:
        the first section defines a plurality of first section loops forming a three-dimensional non-helical structure configured to anchor the device body in vasculature of a patient, each second section of the two or more second sections defines a plurality of second section loops forming a three-dimensional non-helical structure, each second section of the two or more second sections has a maximum cross-sectional dimension that is smaller than a maximum cross-sectional dimension of the first section, and the third section defines a third section loop configured to exert a larger radial force against a vessel wall compared to at least one of the first or second sections, the third section loop facing a distal direction, wherein the device body defines a longitudinal axis extending in a direction from the third section to the two or more second sections, and wherein the two or more second sections are spaced from each other along the longitudinal axis, such that at least one second section trails another second section.

15. The medical device of claim 14, wherein the maximum cross-sectional dimension of the first section is from about 10% to about 100% larger than the maximum cross-sectional dimension of each second section.

16. The medical device of claim 14, wherein the third section defines a helical structure.

17. The medical device of claim 14, wherein the third section loop is larger than at least one first section loop of the plurality of first section loops.

18. A medical device comprising:
a device body comprising a first section, two or more second sections connected to one end of the first section, and a third section connected to the other end of the first section distal to the first section, wherein, in a first configuration of the device body, the device body has a longitudinally extending configuration, and wherein, in a second, deployed configuration of the device body:

the first section defines a plurality of first section loops forming a three-dimensional non-helical structure configured to anchor the device body in vasculature of a patient, each second section defines a plurality of second section loops forming a three-dimensional non-helical structure, each second section has a maximum cross-sectional dimension that is smaller than a maximum cross-sectional dimension of the first section, and the third section defines a third section loop configured to exert a larger radial force against a vessel wall compared to at least one of the first or second sections, the third section loop being larger than at least one first section loop of the plurality of first section loops, wherein the device body defines a longitudinal axis extending in a direction from the third section to the two or more second sections, and wherein the two or more second sections are spaced from each other along the longitudinal axis, such that at least one second section trails another second section.

19. The medical device of claim 18, wherein the three-dimensional non-helical structure of at least one of the first section or each second section being an approximately polyhedral structure having three or more sides.

20. A medical device comprising:
a device body comprising:
a first section;
a plurality of second sections; and
a third section connected to the first section on an opposite side of the first section from the plurality of second sections, wherein the device body defines a longitudinal axis extending in a direction from the third section to the plurality of second sections, and wherein, in a deployed configuration of the device body:

the first section defines a plurality of first section loops forming a three-dimensional non-helical structure configured to anchor the device body in vasculature of a patient, each second section of the plurality of second sections defines a plurality of second section loops forming a three-dimensional non-helical structure, the three-dimensional non-helical structure of at least one of the first section or each second section being an approximately polyhedral structure having three or more sides, the approximately polyhedral structure having three or more sides is defined by six loops, each second section of the plurality of second sections has a maximum cross-sectional dimension that is smaller than a maximum cross-sectional dimension of the first section, and the third section forms a different sized and shaped structure than the three-dimensional non-helical structures formed by the first and second sections and defines a third section loop larger than at least one first section loop of the plurality of first section loops.

21. A medical device comprising:
a device body comprising:
a first section;
a plurality of second sections, wherein the plurality of second sections comprises at least three second sections; and
a third section connected to the first section on an opposite side of the first section from the plurality of second sections, wherein the device body defines a longitudinal axis extending in a direction from the third section to the plurality of second sections, and wherein, in a deployed configuration of the device body:

the first section defines a plurality of first section loops forming a three-dimensional non-helical structure configured to anchor the device body in vasculature of a patient, each second section of the plurality of second sections defines a plurality of second section loops forming a three-dimensional non-helical structure, the three-dimensional non-helical structure of at least one of the first section or each second section being an approximately polyhedral structure having three or more sides, each second section of the plurality of second sections has a maximum cross-sectional dimension that is smaller than a maximum cross-sectional dimension of the first section, and the third section forms a different sized and shaped structure than the three-dimensional non-helical structures formed by the first and second sections and defines a third section loop larger than at least one first section loop of the plurality of first section loops.

* * * * *